United States Patent
Frauenkron et al.

(10) Patent No.: US 7,119,231 B2
(45) Date of Patent: Oct. 10, 2006

(54) METHOD FOR PRODUCING ALKANOLAMINES

(75) Inventors: Matthias Frauenkron, Ludwigshafen (DE); Ulrich Müller, Neustadt (DE); Wolfgang Harder, Weinheim (DE); Jörg Unger, Böhl-Iggelheim (DE); Johann-Peter Melder, Böhl-Iggelheim (DE); Anton Meier, Birkenheide (DE); Walter Himmel, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 87 days.

(21) Appl. No.: 10/297,052

(22) PCT Filed: Jun. 7, 2001

(86) PCT No.: PCT/EP01/06481

§ 371 (c)(1),
(2), (4) Date: Dec. 2, 2002

(87) PCT Pub. No.: WO01/94290

PCT Pub. Date: Dec. 13, 2001

(65) Prior Publication Data

US 2003/0149305 A1    Aug. 7, 2003

(30) Foreign Application Priority Data

Jun. 9, 2000 (DE) .............................. 100 28 636

(51) Int. Cl.
C07C 213/04 (2006.01)
(52) U.S. Cl. ...................... 564/475; 564/477
(58) Field of Classification Search ........... 564/475, 564/477
See application file for complete search history.

(56) References Cited

U.S. PATENT DOCUMENTS

| 3,697,598 | A | | 10/1972 | Weibull et al. ............ 260/584 |
| 4,438,281 | A | * | 3/1984 | Johnson, Jr. ............... 564/477 |
| 4,939,301 | A | * | 7/1990 | Grice et al. ................. 564/477 |
| 5,846,453 | A | | 12/1998 | Mohr et al. ................ 252/331 |
| 6,063,965 | A | * | 5/2000 | Nygaard et al. ........... 564/477 |
| 6,235,940 | B1 | | 5/2001 | Mohr et al. ................ 564/468 |

FOREIGN PATENT DOCUMENTS

| DE | 1 941 859 | 3/1970 |
| DE | 25 47 328 | 4/1976 |
| DE | 298 636 | 3/1992 |
| EP | 0 652 207 | 5/1995 |
| EP | 0 941 986 | 9/1999 |
| GB | 1 529 193 | 10/1978 |
| WO | WO 96/11225 | 4/1996 |
| WO | WO 96/22274 | 7/1996 |
| WO | WO 99/33783 | 7/1999 |
| WO | WO 00/32553 | 6/2000 |

* cited by examiner

*Primary Examiner*—Brian Davis
(74) *Attorney, Agent, or Firm*—Novak Druce & Quigg LLP

(57) ABSTRACT

At least one alkanolamine is prepared by reacting ammonia with alkylene oxide in a reaction space in the presence of a catalyst to give monoalkanolamine or dialkanolamine or trialkanolamine or a mixture of two or three of these compounds, the distribution of the various alkanolamines within the product spectrum being controlled by means of the temperature in the reaction space, by a process in which the temperature is established by regulating the temperature profile in the reaction space.

13 Claims, No Drawings

METHOD FOR PRODUCING ALKANOLAMINES

This application is a 371 of PCT/EP01/06481 filed Jun. 7, 2001.

The present invention relates to a process for the preparation of alkanolamines from alkylene oxide and ammonia, the novel process being distinguished by the fact that the selectivity of the reaction can be influenced by specifically controlling the temperature of the reaction space, this control being effected by regulating the temperature profile in the reaction space. In a particularly preferred embodiment, the present invention relates to a process for carrying out the reaction flexibly in the preparation of alkanolamines, which process is distinguished by the fact that the product selectivities of the alkanolamine synthesis can be established by the above mentioned measure of specific temperature regulation in a reaction space in the presence of the same catalyst. In an embodiment which is likewise preferred, the present invention relates to a process for the preparation of dialkanolamines, in which monoalkanolamine is prepared selectively in a first process stage and dialkanolamine is prepared selectively from this monoalkanolamine in a second process stage.

DE-A 19 41 859.8 describes a process for the selective synthesis of monoalkanolamines from alkylene oxide and ammonia in the presence of a cation-exchange resin. For optimum utilization of the plant, the temperature of the reaction volume of the catalyst and the flow rate of the reaction mixture through the catalyst are established so that the highest yields of monoalkanolamine per unit time can be achieved.

EP-A 0 652 207 discloses a process for the preparation of monoalkanolamines from alkylene oxides and ammonia in the liquid phase, the catalyst used being one which comprises a rare earth element which is applied to a heat-resistant support. For example, the preparation of monoethanolamine is described explicitly. The temperature at which the reaction takes place is determined only by the temperature of the oil bath, as is evident from the examples.

EP-A 0 941 986 describes a process for the preparation of dialkanolamines starting from alkylene oxide and ammonia, zeolite catalysts being used. Here too, the temperature at which the reaction takes place is only determined roughly via the temperature of the oil bath.

DD 298 636 describes a process for the preparation of diethanolamine by reacting ammonia and ethene oxide in the gas phase, the catalyst used being a heterogeneous catalyst, a crystalline silicate of the pentasil type.

DE-A 25 47 328 describes a process for the continuous preparation of dialkanolamines, in which, in a first reaction zone, an olefin oxide is brought into contact with ammonia, the monoalkanolamine formed is separated from the material removed from the first reaction zone and the monoalkanolamine separated off is brought into contact in a second reaction zone with an olefin oxide. The trialkanolamine preparation is regulated by establishing the molar ratio of monoalkanolamine to olefin oxide, and the reactions take place with exclusion of water in the absence of a catalyst.

It is an object of the present invention to provide a process which makes it possible to establish and to control the product selectivity very exactly and hence to have a process which, inter alia, can be adapted flexibly and rapidly to a specific product demand and/or permits high product selectivities.

We have found that this object is achieved by a process for the preparation of at least one alkanolamine by reacting ammonia with alkylene oxide in a reaction space in the presence of a catalyst to give monoalkanolamine or dialkanolamine or trialkanolamine or a mixture of two or three of these compounds, the distribution of the various alkanolamines in the product spectrum being controlled by means of the temperature in the reaction space, wherein the temperature is established by regulating the temperature profile in the reaction space.

In the context of the present invention, the term reaction space denotes reactors, reactor compartments and reactor sections. An individual reactor can therefore constitute both a single reaction space and, if this individual reactor is divided into two or more sections, if necessary sections or compartments physically separated from one another, for process engineering reasons, two or more different reaction spaces. The term reaction space also includes those embodiments in which two or more reactors, for example connected in parallel or in series, constitute a single reaction space.

The regulation of the temperature profile in the reaction space can be carried out by all suitable methods. For example, it is possible to start from a specific setpoint value of the temperature profile, the actual value determined by suitable methods being compared with this setpoint value and the actual value being adapted iteratively or directly, discretely or continuously, to this setpoint value by suitable methods. It is also possible to change the setpoint value of the temperature profile taking into account, for example, the product spectrum obtained and to adapt the actual value to the respective different setpoint values and hence to variable setpoint values. In the context of the present application, the term setpoint value denotes that value of the temperature profile for which a specific desired distribution of the alkanolamines in the product spectrum is obtained. In the context of the present application, the term actual value denotes that value of the temperature profile which is determined by suitable methods and is adapted to the setpoint value. In the context of the present application, the term value of the temperature profile denotes the totality of the measured values which are determined by suitable methods of measurement and establish the temperature profile in the reaction space.

The temperature or the temperature profile is regulated essentially by adapting the heat flows from the reaction space into the insulation means surrounding the reaction space, for example a double-jacket cooling tube surrounding the reaction space. In this embodiment, as also stated below, a plurality of double-jacket cooling tubes are more preferably used in succession along the reaction space, for example a tubular reactor. These are loaded independently of one another with cooling liquid. This arrangement facilitates the flexible control of the temperature profile. For a specific reactor design and reactant flows of fixed compositions, control parameters are the volume flow rates of the coolant and the inlet temperatures in the insulation means, for example the double jacket, or into the successive double jackets around the reactor.

The variable flow rate of the coolant is realized, for example, by controlling corresponding circulation pumps. The different temperature of the coolant on entering the insulation means can be varied within wide limits by means of one or more secondary circulations having heat exchangers.

The temperature profile in the reaction space can be obtained in general by any suitable method. In particular, the number and position of the measuring points at which the temperature is determined can be adapted to the geometry and size of the reaction space. In this context, the temperature profile in the reaction space can therefore be determined with any desired accuracy corresponding to the requirements.

The temperature measurements per se can be carried out here by any suitable method.

For the temperature measurement, all conventional temperature sensors can be used in the interior of the reaction space, it being possible to use, for example, thermocouples or resistance thermometers with or without a protective tube. For the temperature measurement at the inlet and outlet of the cooling medium in the insulation means, sensors of the same type are preferably used. In addition, optical, contactless methods for measuring the heat radiation can be used at the outer limit of the insulation means for the temperature measurement or the measurement can be effected by means of thermocouples or resistance thermometers by a contact method at the outer limit of the insulation means. Preferably, the temperature measurement is carried out in the interior of the reaction space in thermal protective tubes. The sensors used are either thermocouples or resistance thermometers, depending on the process control system.

In the process according to the invention, particularly preferred measured variables for temperature control are the temperature gradient and that location in the reaction space at which the maximum temperature is reached. In this context, the term temperature gradient is understood as meaning the temperature difference between the maximum temperature in the reactor and the temperature of the starting material stream or of the starting material streams. Accordingly, if two or more starting material streams at different temperatures are passed into the reaction space, it is possible that, starting from a maximum temperature, two or more different temperature gradients are used for temperature control. Depending on the geometry and/or size of the reaction space, it is also possible that there are in the reaction space two or more locations at which in each case the same maximum temperatures occur within the accuracy of measurement and/or the accuracy requirements of the procedure.

Regarding the stress on the material of the reactor, it is particularly advantageous not to use a particularly hot reaction zone which is sharply limited spatially but a balanced temperature gradient over the length of the tube. In addition, the choice of the hotspot temperature and of the location of the hotspot along the desired ratio of the products is advantageous. They are obtained from the choice of the volume flow rates (residence times) and the temperature level thus established in the reactor.

The present invention therefore also relates to a process, as described above, wherein the regulation of the temperature profile in the reaction space is effected by establishing the temperature gradient in the reaction space in a controlled manner or by establishing the location of the maximum temperature in the reaction space in a controlled manner or by establishing both parameters in a controlled manner.

The temperature gradient describes the local change in the temperature along the reaction zone. For this purpose, a plurality of temperature sensors are distributed along this zone in the reaction space. With said sensors, the local change in the temperature and its maximum value, the hotspot, can be determined, regulation being effected as described further above herein.

The temperature profile which occurs and is regulated in the reaction space in the novel process can be influenced by all suitable measures.

For example, the heat generated in the course of the reaction can be removed by any suitable method in order to reduce the temperature. Inter alia, external cooling, for example by one or more cooling jackets which surround the reaction space, is possible. It is also possible to remove the evolved heat of reaction by passing one or more suitable inert gases through the reaction space. Heat of reaction can also be removed, for example, by evaporating a part of the ammonia present in the reaction space. All suitable methods can likewise be used for increasing the temperature in the reaction space. These include both direct methods, for example heating the reaction space from outside, and indirect methods. Indirect methods are understood as meaning, inter alia, those methods in which a temperature increase is achieved by complete or partial reduction of the temperature-reducing measures described above.

If necessary for regulating the temperature profile in the novel process, the temperature can be increased in one or more sections and the temperature can be simultaneously reduced in one or more sections, depending on the geometry of the reaction space.

Further possibilities for influencing the temperature in the reaction space are by means of the residence time of the reactants in the reaction space, the flow rate of the reaction mixture through the reaction space in a continuous procedure or the temperature of the starting material stream or of the starting material streams which are passed into the reaction space.

Preferably, the temperature profile is determined by the liberated chemical energy with corresponding heating-up of the reactant stream and regulated by physical heat removal by radiation or more effectively by heat removal by means of a cooling medium. For this purpose, reference is also made to the above detailed description relating to the specific control of the heat removal using a cooling means which makes it possible to control the heat removal within wide limits.

The group of reactants as used above includes all compounds which react with one another in the course of the novel process. These are in particular alkylene oxide, ammonia and alkanolamine. Further examples are monoalkanolamine, which can react with alkylene oxide to give dialkanolamine, and dialkanolamine, which can react with alkylene oxide to give trialkanolamine.

Of course, all these measures can also be combined with one another in a suitable manner. An example of a further method, which can likewise be combined with the above-mentioned measures, involves the molar ratio of the starting materials ammonia and alkylene oxide. In this very particularly preferred embodiment of the novel process, the distribution of the various alkanolamines in the product spectrum is accordingly controlled by the molar ratio of the starting materials of the reaction which are passed into the reaction space.

The present invention also relates to a process, as described above, wherein the distribution of the various alkanolamines in the product spectrum is additionally controlled through the molar ratio of ammonia to alkylene oxide.

It is also possible in principle to influence the distribution of the various alkanolamines in the product spectrum additionally by means of the pressure under which the reaction is carried out.

In general, there are no restrictions with regard to the geometry and the size of the reaction space. For example, it is possible in particular to use stirred kettles, stirred kettle cascades, tubular reactors, tubular reactor cascades or reactive distillation columns as suitable reaction spaces. Moreover, both batchwise and continuous procedures are possible. Combinations of batchwise and continuous procedures and combinations of different reactor forms, which in turn can be connected in series and/or in parallel, are also possible.

In a particularly preferred embodiment of the novel process, tubular reactors are used for reacting alkylene oxide with ammonia. In this context, two or more tubular reactors may be connected in series or two or more tubular reactors can be connected in parallel or a combination of serial and parallel arrangements may be provided.

The present invention therefore also relates to a process, as described above, wherein the reaction is carried out in a tubular reactor.

The tubular reactor used according to the invention is, for example, a pressure-resistant reaction tube which can be divided logically or physically into individual sections. The sections are thermostated either together or individually, independently of one another, for example by coolant circulations surrounding them, i.e. by, for example, double-jacket tubes or other constructive measures determining the heat flow. In the individual sections, the temperature is determined by a plurality of temperature sensors, i.e. at least two temperature sensors.

The constructional arrangement of the sections can also be realized in a manner such that the reaction mixture flows successively through a plurality of reaction tubes arranged concentrically one inside the other so that the heat removed is transferred not only to the cooling medium in the surrounding double-jacket tubes but also or instead serves for heating the reaction mixture itself.

The reaction as such is carried out in general in the presence of a catalyst.

The use of a homogeneous catalyst, for example water or an alkanolamine, is generally possible. Inter alia, suitable inorganic or organic acids or ammonium salts may be mentioned here.

In the novel process, a heterogeneous catalyst is particularly preferably used. Of course, two or more suitable heterogeneous catalysts may also be used. Furthermore, zeolite-analogous materials, for example aluminophosphates and silicoaluminophosphates, and organic ion exchangers, as described, for example, in DE-A 19 41 859.8, can be used.

In a very particularly preferred embodiment, a zeolite catalyst is used as the one or more heterogeneous catalysts. In the context of the present invention, the term zeolite catalyst denotes all oxides which are suitable as catalysts and have or comprise a zeolite structure or a zeolite-analogous structure.

The present invention therefore also relates to a process, as described above, wherein the reaction is carried out in the presence of a heterogeneous catalyst, preferably of a heterogeneous zeolite catalyst.

The catalyst preferably used according to the invention is preferably an oxide, comprising at least the elements Si and Ti, at least noncrystalline silica and at least one crystalline silicate phase which has at least one zeolite structure, noncrystalline silica being applied to at least one crystalline silicate phase which has at least one zeolite structure, wherein the oxide has no silicon-carbon bonds.

Zeolites as such are known to be crystalline aluminosilicates having ordered channel and cage structures which have micropores. The term micropores as used in the context of the present invention corresponds to the definition in Pure Appl. Chem. 57 (1985), 603–619, and denotes pores having a pore diameter of less than 2 nm. The network of such zeolites is composed of $SiO_4$ and $AlO_4$ tetrahedra which are linked by common oxygen bridges. An overview of the known structures is to be found, for example, in W. M. Meier, D. H. Olson and Ch. Baerlocher in Atlas of Zeolite Structure Types, Elsevier, 4th Edition, London 1996.

There are in particular zeolites which contain no aluminum and in which some of the Si(IV) in the silicate lattice has been replaced by titanium as Ti(IV). The titanium zeolites, in particular those having a crystal structure of the MFI type, and possibilities for their preparation are described, for example, in EP-A 0 311 983 or EP-A 0 405 978.

It is known that titanium zeolites having an MFI structure can be identified by means of a specific pattern in the determination of their X-ray diffraction patterns and additionally by means of a skeletal vibration band in the infrared region (IR) at about 960 $cm^{-1}$ and thus differ from alkali metal titanates or crystalline and amorphous $TiO_2$ phases.

Specific examples of the catalysts preferably used in the novel process are zeolites having a pentasil structure, in particular those having structures ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG, ZON or a mixed structure comprising two or more of these structures and ITQ-4, ITQ-6, ITQ-7 and CIT-6. A large number of these zeolites of this type are described, for example, in the abovementioned publication by Meier et al.

The oxide used according to the invention as a catalyst may furthermore comprise titanium-containing zeolites having the UTD-1, CIT-1, CIT-5, MCM-22 or MCM-61 structure. Examples of further titanium-containing zeolites are those having the ZSM-48 or ZSM-12 structure. Such zeolites are described, inter alia, in U.S. Pat. No. 5,430,000 and WO 94/29408, the content of which in this context is hereby included by reference in its entirety in the present application. In the context of the present invention, Ti zeolites having the MFI, MEL or MFI/MEL mixed structure are to be regarded as being particularly preferred. Ti zeolites having a skeletal structure isomorphous with beta-zeolite may also be mentioned as being preferred.

In addition to silicon and titanium, the one or more crystalline silicate phases having at least one zeolite structure may also contain additional elements, e.g. aluminum, zirconium, vanadium, tin, zinc, iron, tellurium, niobium, tantalum, chromium, cobalt, nickel, gallium, germanium, boron or small amounts of fluorine.

Preferably, the novel oxide comprises titanium, vanadium, chromium, niobium and zirconium zeolites, more preferably titanium zeolites and in particular titanium silicalites.

Regarding the pore structure of the one or more crystalline silicate phases having a zeolite structure, there are no particular restrictions in this context. For example, structures having micropores, mesopores or macropores or having micropores and mesopores or having micropores and macropores or having micropores and mesopores and macropores are possible, the definition of these pores in the context of the present invention corresponding to the definition in Pure Appl. Chem. 45, 71 et seq. and characterizing micropores having a diameter of less than or equal to 2 nm, mesopores having a diameter greater than 2 nm to about 50 nm and macropores having a diameter of greater than 50 nm.

Regarding the preparation process for the novel oxide, there are essentially no restrictions provided that the novel oxide is obtained from this process. Preferably, the oxide is prepared in a process in which a suitable oxidic material which has at least one crystalline silicate phase having a zeolite structure is treated with a suitable silane or silane derivative.

The present invention therefore also relates to a process, as described above, wherein the catalyst is a silylated zeolite catalyst.

This catalyst is preferably obtained by a process for the preparation of an oxide comprising at least the elements Si and Ti, at least noncrystalline silica and at least one crystalline silicate phase, in which
(a) an oxidic material comprising at least the elements Si and Ti and at least one crystalline silicate phase which has at least one zeolite structure is prepared and
(b) the oxidic material obtained from (a)
   (i) is reacted, in at least one solvent, with at least one silane or at least one silane derivative or with a mixture of two or more thereof to give a mixture comprising at least one oxidic reaction product and the one or more solvents,
      the one or more solvents are removed from the mixture directly after the reaction, to give the one or more oxidic reaction products, and
      the one or more oxidic reaction products are calcined directly after the removal of the one or more solvents, to give the oxide, or
   (ii) are reacted in the gas phase with at least one silane or at least one silane derivative or a mixture of two or more thereof to give at least one oxidic reaction product and the one or more oxidic reaction products are calcined directly after the reaction, to give the oxide.

Details of this process appear in DE-A 199 54 322.4, which is hereby incorporated by reference in the context of the present application.

In a preferred embodiment, the one or more silanes or the one or more silane derivatives are selected from the group consisting of trichlorosilane, silicon tetrachloride, methylhydrogendichlorosilane, mono-, di- and trimethylchlorosilane, tetraalkyl orthosilicates having identical or different alkyl radicals of more than 2 carbon atoms, hydrolysis products of these tetralkyl orthosilicates, alkylalkoxysilanes having identical or different alkyl radicals and alkoxy radicals, and the abovementioned silanes or silane derivatives which additionally have one or more functional groups selected from the group consisting of hydroxyl, carboxyl, vinyl, glycidyl, amino and aminoalkyl groups.

Particularly preferred in the context of the present invention are those silanes or silane derivatives which have at least one silicon-carbon bond. The one or more silanes or the one or more silane derivatives are therefore preferably selected from the group consisting of methylhydrogendichlorosilane, mono-, di- and trimethylchlorosilane, tetraalkyl orthosilicates having identical or different alkyl radicals of more than 2 carbon atoms, hydrolysis products of these tetralkyl orthosilicates, alkylalkoxysilanes having identical or different alkyl radicals and alkoxy radicals, and the abovementioned silanes or silane derivatives, which additionally have one or more functional groups selected from the group consisting of hydroxyl, carboxyl, vinyl, glycidyl, amino and aminoalkyl groups.

Also very particularly preferably, an oxidic material in the form of a molding, produced from titanium silicalite having the TS-1 structure and a silica binder, is reacted with 3-aminopropyltriethoxysilane, dissolved in a suitable anhydrous solvent.

Preferably, the novel catalyst is used in a fixed bed. Stacked or structured packing and thin-film catalysts are other examples of forms which may be used.

This novel, preferably used heterogeneous zeolite catalyst can be regenerated in the novel process generally by any suitable method. Such methods are described, for example, in DE-A 100 15 246.5, which is hereby incorporated by reference in the context of the present application.

In general, all suitable alkylene oxides may be used in the novel process, in particular those having the structure $R_1R_2COCR_3R_4$ being preferred. Here, $R_1$ to $R_4$ are identical or different and are each hydrogen, methyl or ethyl. Alkylene oxides of 2 to 4 carbon atoms are particularly preferably used, ethylene oxide in turn being preferably used.

The present invention therefore also relates to a process, as described above, wherein the alkylene oxide used is ethylene oxide.

Here, the alkylene oxide can be prepared in principle by any suitable process and used in the novel process. Such processes are part of the prior art and are described in detail, inter alia, in Ullmann's Enzyclopädie der Technischen Chemie (5th Edition). Furthermore, reference is made to the preparation processes for alkylene oxide and in particular for propylene oxide, as described, inter alia, in PCT/EP99/05740 and DE-A 100 15 246.5, which is hereby incorporated by reference in its entirety in the context of the present application.

In a preferred embodiment, the alkylene oxide used according to the invention as starting material is prepared by reacting the corresponding alkene with a hydroperoxide, oxygen-containing gas or pure oxygen.

The present invention therefore also relates to a process, as described above, wherein the alkylene oxide is prepared by reacting an alkene with a hydroperoxide.

If, for example, propylene oxide is used as a starting material, it is preferably prepared by reacting propene with hydrogen peroxide. The reaction with hydrogen peroxide is more preferably effected in the presence of a catalyst, preferably of a heterogeneous catalyst, more preferably of a catalyst which has a zeolite structure. Regarding the possible zeolite structures, reference may be made to the structures described above. An example of a particularly preferred catalyst is one having the structure TS-1. In this context, reference is made to the above-mentioned publications PCT/EP99/05740 and DE-A 100 15 246.5.

Regarding the preparation of the preferably used ethylene oxide, reference is made to Ullmann's Encyclopadie der Technischen Chemie (loc. cit.).

If monoalkanolamine is preferably to be prepared in the novel process, the product stream from the reaction space, which may contain dialkanolamine and/or trialkanolamine and ammonia and water in addition to the monoalkanolamine, can be fed to one or more separation stages in which this mixture is separated. In a preferred embodiment, first the low-boiling components, for example ammonia and water, are separated off and then, if required, the monoalkanolamine is separated from dialkanolamine and/or trialkanolamine, preferably by distillation. Here, the distillation can be carried out by any suitable method.

The mono-, di- and triethanolamines can be separated off by conventional methods. Distillation is preferred, but liquid/liquid extraction or separations by membrane are also used.

The components separated off, such as ammonia or water, can then be recycled to the process in which monoalkanolamine is preferably prepared. Monoalkanolamine separated off can be obtained as a desired product or can be wholly or partly fed to a process in which di- or trialkanolamine is preferably prepared and in which the monoalkanolamine serves as a starting material.

If dialkanolamine is preferably prepared in the novel process, the product stream from the reaction space, which may contain monoalkanolamine and/or trialkanol-amine and ammonia and water in addition to the dialkanolamine, can be fed to one or more separation stages in which this mixture is separated. In a preferred embodiment, once again first the low-boiling components, for example ammonia and water, are separated off and then, if required, the dialkanolamine is separated from monoalkanolamine and/or trialkanolamine, preferably by distillation. Here, the distillation can once again be effected by any suitable method.

The components separated off, such as monoalkanolamine, ammonia or water, can then be recycled to the process in which dialkanolamine is preferably prepared. Dialkanolamine separated off can be obtained as a desired product or can be fed wholly or partly to a process in which trialkanolamine is preferably prepared and in which the dialkanolamine serves as a starting material.

If trialkanolamine is preferably prepared in the novel process, the product stream from the reaction space, which may contain monoalkanolamine and/or dialkanol-amine and ammonia and water in addition to trialkanolamine, can be fed to one or more separation stages in which this mixture is separated. In a preferred embodiment, once again first the low-boiling components, for example water and ammonia, are separated off and then, if required, the trialkanolamine is separated from monoalkanolamine and/or dialkanolamine, preferably by distillation. Here once again, the distillation can be effected by any suitable method.

The components separated off, such as monoalkanolamine, dialkanolamine, ammonia or water, can then be recycled to the process in which trialkanolamine is preferably prepared. Monoalkanolamine separated off can also be fed to a further process in which dialkanolamine is preferably prepared and in which the monoalkanolamine serves for a starting material.

The mono-, di- and triethanolamines can be separated off by conventional methods. Distillation is preferred but liquid/liquid extraction or separations through membranes are also used.

An advantage of the novel control of the distribution of the various alkanolamines in the product spectrum by regulating the temperature profile in the reaction space is, inter alia, that the process can be designed to be substantially more flexible than the processes described in the prior art. Whereas in the prior art the processes or the catalysts described in this context were optimized so that either monoalkanolamine or dialkanolamine or trialkanolamine can be prepared in a specific yield, the novel process permits, through the specific temperature regulation inter alia, preferably in combination with the regulation of the molar ratio of the starting materials ammonia and alkylene oxide, a procedure in which mono- or di- or trialkanolamine is first preferably prepared in a single reaction space in the presence of the same catalyst in a first process stage and an alkanolamine which is different from the alkanolamine preferably prepared in the first process stage is preferably prepared in a second process stage through the novel regulation.

By means of this flexible procedure, it is possible, for example, to respond in a variable manner to customers' wishes or to adapt the process to changing market conditions without great expense.

The present invention therefore also relates to a process, described above, wherein
(i) in a first process stage, monoalkanolamine or dialkanolamine or trialkanolamine is selectively prepared and
(ii) in a second process stage in the same reaction space and in the presence of the same catalyst, by regulation of the temperature profile in the reaction space and, if required, additionally through the molar ratio of ammonia to alkylene oxide, the product selectivity in the second process stage is changed in comparison with the first process stage.

Of course, this embodiment of the process also comprises procedures in which, in at least one additional process stage, likewise in the same reaction space and likewise in the presence of the same catalyst, by regulation of the temperature profile in the reaction space and, if required, additionally through the molar ratio of ammonia to alkylene oxide, the product selectivity in this at least one additional process stage is changed in comparison with the second or generally with the respective preceding process stage.

Further possibilities for likewise influencing the distribution of the various alkanolamines in the product spectrum by additional measures are described above and can also be used in the flexible process described here.

In the novel process, monoalkanolamines are generally prepared at from 20 to 250, preferably from 40 to 230, particularly preferably from 70 to 160, bar. The temperature of the ammonia stream as well as the temperature of the alkylene oxide stream, which are passed into the reaction space, is in general from 20 to 200° C., preferably from 50 to 150° C., particularly preferably from 60 to 140° C. Here, the molar ratio of ammonia to alkylene oxide is in general from 100 to 7, preferably from 40 to 7, particularly preferably from 20 to 7. The maximum temperature in the reaction space is furthermore generally less than 200° C., preferably from 20 to 180° C., more preferably from 50 to 150° C., particularly preferably from 60 to 130° C.

In the novel process, dialkanolamines are generally prepared at from 20 to 250, preferably from 40 to 230, particularly preferably from 70 to 160, bar. The temperature of the ammonia stream as well as the temperature of the alkylene oxide stream, which are passed into the reaction space, is in general from 20 to 180° C., preferably from 40 to 150° C., particularly preferably from 60 to 140° C. Here, the molar ratio of ammonia to alkylene oxide is in general from 10 to 2, preferably from 8 to 2, particularly preferably from 7 to 2. The maximum temperature in the reaction space is furthermore generally from 70 to 200° C., preferably from 75 to 150° C., particularly preferably from 80 to 140° C.

In the novel process, trialkanolamines are generally prepared at from 5 to 250, preferably from 30 to 230, particularly preferably from 40 to 160, bar. The temperature of the ammonia stream as well as the temperature of the alkylene oxide stream, which are passed into the reaction space, is generally from 20 to 180° C., preferably from 40 to 150° C., particularly preferably from 60 to 140° C. Here, the molar ratio of ammonia to alkylene oxide is in general from 10 to 0.3, preferably from 8 to 0.3, particularly preferably from 6 to 0.3. The maximum temperature in the reaction space is furthermore generally less than 400° C., more preferably from 75 to 400° C., even more preferably from 90 to 400° C., particularly preferably from 100 to 400° C.

This procedure can be carried out essentially for all alkylene oxides which are described above and can be used as starting materials. For the purposes of the present invention, a preferably used starting material is ethylene oxide.

The present invention therefore relates to a process, as described above, wherein
(i) in a first process stage, monoethanolamine or diethanolamine or triethanolamine is selectively prepared and
(ii) in a second process stage, in the same reaction space and in the presence of the same catalyst, by regulation of the temperature profile in the reaction space and, if required, additionally through the molar ratio of ammonia to ethylene oxide, the product selectivity in the second process stage is changed in comparison with the first process stage.

In connection with this preferred embodiment of the novel process, in which, in a first process stage, monoethanolamine or diethanolamine or triethanolamine is selectively prepared and, in a second process stage, in the same reaction space and in the presence of the same catalyst, by regulation of the temperature profile in the reaction space and, if required, additionally through the molar ratio of ammonia to ethylene oxide, the product selectivity in the second process stage is changed in comparison with the first process stage, the term selectivity is used as follows:

the desired product monoethanolamine is selectivity prepared when more than 65% by weight of monoethanolamine are present in the product spectrum;
the desired product diethanolamine is selectively prepared when more than 35% by weight of diethanolamine are present in the product spectrum;
the desired product triethanolamine is selectively prepared when more than 35% by weight of triethanolamine are present in the product spectrum.

The data in % by weight are based in each case on the total amount of the ethanolamines prepared.

Accordingly, the present invention also relates to a process, as described above, wherein
(a) more than 65% by weight of monoethanolamine are formed in (i) and more than 35% by weight of di- or triethanolamine are formed in (ii) or
(b) more than 35% by weight of di- or triethanolamine are formed in (i) and more than 65% by weight of monoethanolamine are formed in (ii), based in each case on the total amount of mono-, di- and triethanolamine.

Regarding the novel procedure, it should be noted that the pressure is chosen at least so that the fluid reaction mixture is present as a single phase without the presence of a gas phase. On the basis of thermodynamics, the resulting minimum pressure is the vapor pressure of the reaction mixture at the corresponding temperature, i.e. said minimum pressure is determined by the concentration of the components and the temperature in individual reactor section.

It is advantageous, but not essential, that the reactor be operated at a single pressure in its total volume. Otherwise, for example, sections with decreasing system pressure are possible and easy to realize, the minimum pressure being determined by thermodynamics, for example by the concentration of the lowest-boiling components in the reaction mixture at the temperature of the hotspot.

If monoethanolamine is prepared in the novel process, for example in a first process stage, in general a pressure of from 20 to 250, preferably from 40 to 230, particularly preferably from 70 to 160, bar is employed. The residence times of the reaction medium in the reactor are in general from 2 to 60, preferably from 5 to 20, minutes. The molar ratio of ammonia to ethylene oxide is in general from 5 to 100, preferably from 5 to 40, more preferably from 5 to 20, mol. Here, temperature gradients, i.e. temperature differences between maximum temperature in the reaction space and the temperature of the unmixed starting materials, which are in the range of, in general, from 0 to 100° C., preferably from 0 to 80° C., more preferably from 0 to 30° C., are employed.

If diethanolamine is to be selectively prepared in the second process stage in the same reaction space in the presence of the same catalyst, temperature gradients which are in the range of, in general, from 50 to 120° C., preferably from 60 to 100° C., are employed in the pressure ranges and residence time ranges which are chosen in the case of the preparation of monoethanolamine.

If triethanolamine is to be selectively prepared in the second process stage in the same reaction space in the presence of the same catalyst, temperature gradients which are in the range of, in general, from 70 to 300° C. are employed in the pressure ranges and residence time ranges which are chosen in the case of the preparation of monoethanolamine and/or of diethanolamine.

The reactions described here, using the stated reaction parameters, relate to the non-back-mixing tubular reactors preferably used according to the invention but may also be applied or transferred to stirred kettles or arrangements of stirred kettles into stirred kettle cascades, which can likewise be used.

Of course, the novel process is not restricted to embodiments in which the reaction is carried out in a single reaction space. Rather, the control of the distribution of the various alkanolamines in the product spectrum by regulation of the temperature profile in the reaction space can be applied to all possible procedures. These also include processes in which an alkanolamine is prepared in a first process stage in a first reaction space in the presence of a first catalyst by reacting an alkylene oxide with ammonia and the alkanolamine obtained is further reacted in a second process stage in a second reaction space. Furthermore, a third process stage and very generally any desired number of further process stages may also follow the second process stage.

Regarding the further reactions, in the second or a further process stage, of the alkanolamine prepared according to the invention in the first process stage, all reactions to which the alkanolamine can be subjected are generally possible.

Preferred procedures of the novel process include those in which an alkylene oxide is reacted with ammonia to give monoalkanolamine in a first process stage in a first reaction space in the presence of a first catalyst and the monoalkanolamine obtained in the first process stage is reacted with alkylene oxide in a second process stage in a second reaction space to give the dialkanolamine and/or to give the trialkanolamine. Here, the monoalkanolamine can be reacted in the second process stage with the same alkylene oxide which was used in the first process stage. In this way, it is possible to prepare symmetrical di- or trialkanolamines. The monoalkanolamine can also be reacted in the second process stage with an alkylene oxide which is different from the alkylene oxide used in the first process stage. If, for example, an asymmetrical dialkanolamine is accordingly prepared in a second process stage, it can in turn be reacted in a third process stage with an alkylene oxide which is identical to or different from one of the alkylene oxides used in the first and/or second process stage. It is also possible to prepare, for example, symmetrical dialkanolamine in the first process stage and to react it with alkylene oxide in a second process stage, the alkylene oxide used in the second process stage being identical to or different from the alkylene oxide used in the first process stage. While it is possible in principle to work without a catalyst in the second process stage, it is particularly preferable to carry out the reaction in the presence of a second catalyst which is identical to or different from the catalyst used in the first process stage.

In a particularly preferred embodiment of the novel process, monoalkanolamine is prepared by reacting alkylene oxide with ammonia in a first process stage in a first reaction space in the presence of a first catalyst. The monoalkanolamine thus obtained is separated from the product mixture and is reacted in a second process stage with the alkylene oxide, which was also used in the first process stage, to give dialkanolamine.

The present invention therefore also relates to a process, as described above, which is referred to below as process II and wherein (I) monoalkanolamine is selectively prepared by reacting ammonia with alkylene oxide in a first process stage in a first reaction space in the presence of a first catalyst, a mixture comprising monoalkanolamine being obtained, (II) monoalkanolamine is separated, in a separation stage, from the mixture obtained from (I), and (III) dialkanolamine is selectively obtained in a second process stage by reacting the monoalkanolamine obtained from (II) with ethylene oxide in a second reaction space in the presence of a second catalyst.

The control of the distribution of the various alkanolamines in the product spectrum by the novel regulation of the temperature profile in the reaction space can be effected here either in (I) or in (III) or in (I) and (III). Preferably, the novel regulation is effected both in process stage (I) and in process stage (III).

Of course, this embodiment of process II also comprises procedures in which, in at least one additional process stage in a further reaction space in the presence of a further catalyst, which may be identical to or different from the catalysts used in (I) and (III), by regulation of the temperature profile in the reaction space and, if required, additionally through the molar ratio of ammonia to alkylene oxide, the product selectivity in this at least one additional process stage can be changed in comparison with the second or generally with the respective preceding process stage.

Further possibilities for influencing the distribution of the alkanolamines in the product spectrum, in addition to the novel regulation of the temperature profile by additional measures, for example the molar ratios of the starting materials of the individual process stages, pressure or residence times of reactants in reaction spaces, are described above and can also be used in process II described here.

This procedure can be carried out essentially for all alkylene oxides which are described above and can be used as starting materials. A preferably used starting material for the purposes of the present invention is ethylene oxide.

The present invention therefore also relates to a process II, as described above, wherein (I) monoethanolamine is selectively prepared by reacting ammonia with ethylene oxide in a first process stage in a first reaction space in the presence of a first catalyst, a mixture comprising monoethanolamine being obtained, (II) monoethanolamine is separated, in a separation stage, from the mixture obtained from (I), and (III) diethanolamine is selectively obtained in a second process stage by reacting the monoethanolamine obtained from (II) with ethylene oxide in a second reaction space in the presence of a second catalyst.

Regarding the catalysts which are used in (I) and (III), these may be identical to or different from one another. Regarding the catalysts which can be used in principle and preferably, reference may be made to the above description.

In this embodiment of the novel process II, monoalkanolamines are generally prepared at pressures which are from 20 to 250, preferably from 40 to 230, particularly preferably from 70 to 160, bar. The temperature of the ammonia stream and the temperature of the alkylene oxide stream, which are passed into the reaction space, are in general from 20 to 200° C., preferably from 50 to 150° C., particularly preferably from 60 to 140° C. The molar ratio of ammonia to alkylene oxide is in general from 100 to 7, preferably from 40 to 7, particularly preferably from 20 to 7. The maximum temperature in the reaction space is furthermore generally less than 200° C., preferably from 20 to 180° C., more preferably from 50 to 150° C., particularly preferably from 60 to 130° C.

The isolation of the monoalkanolamine according to (II) can be carried out by all suitable processes II. Preferably, components of the mixture obtained from (I) which are low-boiling in comparison with monoalkanolamine are first separated off and then the monoalkanolamine is isolated. All separations here are preferably effected by distillation. The low-boiling components separated off, for example ammonia or water, can be recycled after the separation to (I).

The particularly preferred monoethanolamine is isolated from the mixture, obtained from (I), by distillation or rectification methods.

In the second reaction stage (III), the monoalkanolamine obtained from (II) is reacted with alkylene oxide. In the novel process II, this reaction is effected at pressures which are in general from 20 to 250, preferably from 40 to 230, particularly preferably from 70 to 160, bar. The temperature of the monoalkanolamine stream and the temperature of the alkylene oxide stream, which are passed into the second reaction space, are in general from 20 to 180° C., preferably from 40 to 150° C., particularly preferably from 60 to 140° C. The molar ratio of monoalkanolamine to alkylene oxide here is in general from 10 to 2, preferably from 8 to 2, particularly preferably from 7 to 2. The maximum temperature in the reaction space is furthermore generally from 70 to 200° C., more preferably from 75 to 150° C., particularly preferably from 80 to 140° C.

In a preferred embodiment, monoalkanolamine is prepared selectively in (I) and dialkanolamine is prepared selectively in (III). In this preferred embodiment of the novel process II, the term selectivity is used as follows:

the desired product monoalkanolamine is prepared selectively in (I) when more than 70% by weight of monoalkanolamine are present in the product spectrum and the desired product dialkanolamine is prepared selectively in (III) when the weight ratio of diethanolamine to triethanolamine in the discharge is $\geq 2.5$.

The data in % by weight are based in each case on the total amount of the alkanolamines prepared in (I) and in (III).

The present invention accordingly also relates to a process II, as described above, wherein (A) more than 70% by weight of monoethanolamine are formed in (I) and (B) the weight ratio of diethanolamine to triethanolamine in the discharge is $\geq 2.5$ in (III), based in each case on the total amount of mono-, di- and triethanolamine in the product spectrum of the respective process stage.

If, in the novel process II, monoethanolamine is prepared selectively in a first process stage, selectivity being understood as that defined in (A), in general pressures of from 20 to 250, preferably from 40 to 230, particularly preferably from 70 to 160, bar are employed. The residence times of the reaction medium in the reactor are in general from 2 to 60, preferably from 5 to 20, minutes. The molar ratio of ammonia to ethylene oxide is in general from 5 to 100, preferably from 5 to 40, more preferably from 5 to 20, mol. Here, temperature gradients, i.e. temperature differences, between the maximum temperature in the reaction space and the temperature of the unmixed starting materials are employed, which are in general from 0 to 100° C., preferably from 0 to 80° C., more preferably from 0 to 30° C.

If diethanolamine is prepared selectively in a second process stage in a second reaction space in the presence of a second catalyst, selectivity being understood as meaning that defined in (B), in general pressures of from 20 to 150, particularly preferably from 30 to 80, bar are employed. The residence times of the reaction medium in the reactor are in general from 1 to 60, particularly preferably from 1 to 30, in particular from 2 to 10, minutes. The molar ratio of ammonia to ethylene oxide is in general from 20 to 3, preferably from 16 to 4, in particular from 10 to 4.

Here, temperature gradients, i.e. temperature differences, between the maximum temperature in the reaction space and the temperature of the unmixed starting materials are employed, which are in general from 0 to 150° C., preferably from 0 to 70° C., more preferably from 0 to 40° C.

The statements made above regarding pressure, temperature and residence time relate to embodiments of the novel process II which are carried out in tubular reactors or in cascades of stirred kettles through which the flow is continuous, it being possible for these parameters to be adapted by a person skilled in the art by means of routine tests when other reactors are used.

The dialkanolamine obtained in (III) can be isolated from the product mixture, obtained in (III), by any suitable methods. Preferably, this separation is effected by distillation.

If monoalkanolamine is present in the product spectrum from (III), it can be recycled as starting material to (III) in a preferred embodiment.

The Examples which follow illustrate the invention.

EXAMPLES

Example 1

Preparation of catalyst 1

400 g of pentasil zeolite having the structure ZBM-10, prepared according to DE-A 43 23 774.6, was milled using an Alexander unit of sieve mesh size 1 mm.

The milled catalyst was then kneaded together with 100 g of Plural® from Condea and 10 g of formic acid, 400 ml of water being added. After a kneading time of 60 minutes, a further 100 ml of water were added.

After a total kneading time of 75 minutes, the kneaded material was processed in an extruder at 50 bar to give 3 mm extrudates.

The material obtained was then dried for 16 hours at 120° C. and then calcined for 5 hours at 500° C. under air.

Example 2

Preparation of Catalyst 2

16 g of 3-aminopropyltriethoxysilane were dissolved in 1000 ml of anhydrous ethanol, which was predried over a 3 Angstrom molecular sieve, and 100 g of the catalyst according to Example 1 were added in a flask.

The batch was thoroughly mixed at a low speed for 10 hours in a rotary evaporator. The solvent was then evaporated.

The material obtained was heated to 550° C. at a heating rate of 2° C./min and was calcined for 3 hours at 550° C. under air.

Example 3

Preparation of Catalyst 3

This Example corresponds to reference example 3 of EP-A 0 941 986, which is hereby incorporated by reference in the context of the present application.

Example 4

Preparation of Catalyst 4 (La/Montmorillonite)

This Example corresponds to catalyst E of EP-A 0 652 207, which is hereby incorporated by reference in the context of the present application.

Examples 5 to 7

Preparation of Ethanolamines

The feed temperature of the ammonia stream was 70° C. The temperature of the ethylene oxide stream was 25° C. The temperature gradient was chosen so that the steepest temperature rise occurred in the first reactor section comprising 5% of the reaction zone (identical to 5% of the reaction volume). The temperatures in the downstream tubular reactor system comprising from 2 to 7 independently thermostated tube sections were kept constant at desired temperatures of from 90 to 160° C., which were uniform in the individual experiments.

The temperature regulation was effected as described above by adapting the inlet temperature of the individual coolant stream. The temperature was measured at the mixing point and with two thermocouples each in each tube section in the interior of the reaction tube, and the inlet and outlet temperatures of the cooling medium in the double jackets of the tube sections were additionally measured.

Ethylene oxide and ammonia were passed through a tubular reactor having an internal diameter of 4 mm and a length of 3 m at from 110 to 120 bar, the residence time being about 3.3 minutes. The residence times were calculated on the basis of the densities of pure ethylene oxide and pure ammonia under reaction conditions and are based on the volume of the empty tube.

Here, the tubular reactor was filled in each case with 15 g of the catalysts stated in Table 1.

The temperature of the reactor was established by means of a thermostated oil circulation through a double jacket around the reaction tube.

The reaction discharge was analyzed by gas chromatography, the compositions stated in Table 1 being determined.

TABLE 1

| Example | Catalyst | Molar ratio NH₃/EO | Temp./ °C. | Selectivities/ % by weight | | |
|---|---|---|---|---|---|---|
| | | | | MEA | DEA | TEA |
| 5 | 1 | 10 | 90 | 71 | 28 | 1 |
| 6 | 1 | 4 | 90 | 42 | 40 | 17 |
| 7 | 1 | 10 | 160 | 26 | 28 | 46 |

The abbreviations EO, MEA, DEA and TEA represent ethylene oxide, monoethanolamine, diethanolamine and triethanolamine. The selectivity is defined as % by weight of alkanolamine/% by weight of the ethanolamines formed in total.

Example 8

Flexible Preparation of Ethanolamines

This Example was carried out analogously to Examples 5 to 7, a mixture of water and 15% of ammonia being used instead of a catalyst.

TABLE 2

| Example | Catalyst | Molar ratio NH₃/EO | Temp./ °C. | Selectivities/ % by weight | | |
|---|---|---|---|---|---|---|
| | | | | MEA | DEA | TEA |
| 11 | Water, 15% | 6 | 90 | 70 | 23 | 7 |
| 12 | Water, 15% | 6 | 130 | 38 | 37 | 25 |
| 13 | Water, 15% | 6 | 170 | 17 | 28 | 55 |

Examples 9 to 13

Selective Preparation of Diethanolamine (a) Selective Preparation of Monoethanolamine Ethylene oxide and ammonia were passed through a tubular reactor having an internal diameter of 4 mm and a length of 3 m at from 110 to 120 bar, the residence time being about 3.3 minutes. The residence times were calculated on the basis of the densities of pure ethylene oxide and pure ammonia under reaction conditions and are based on the volume of the empty tube.

Here, the tubular reactor was filled in each case with 15 g of the catalysts stated in Table 2.

The temperature of the reactor was established by means of a thermostated oil circulation through a double jacket around the reaction tube, the feed temperature being 70° C.

The reaction discharge was analyzed by gas chromatography, the compositions stated in Table 3 being determined.

TABLE 3

| Example | Catalyst | Molar ratio NH₃/EO | Temp./ °C. | Selectivities/ % | | |
|---|---|---|---|---|---|---|
| | | | | MEA | DEA | TEA |
| 9 | Dowex ® 50X8 | 60 | 100 | 92 | 8 | 0 |
| 10 | 4 | 25 | 95 | 90 | 10 | 0 |
| C1 | 15% by wt. of water | 10 | 100 | 60 | 30 | 10 |

Water was added to the ammonia stream to give a water concentration of 15% by weight in the water-containing ammonia stream. In the further examples, in which the presence of water in the feed was not expressly referred to, anhydrous ammonia was used.

The abbreviations EO, MEA, DEA and TEA represent ethylene oxide, monoethanolamine, diethanolamine and triethanolamine. The selectivity is defined as the ratio of the percentages by weight of the alkanolamines to the sum of the percentages by weight of the ethanolamines formed.

(b) Selective Preparation of Diethanolamine

Monoethanolamine was reacted with ethylene oxide over a fixed bed in the tubular reactor. The reaction was carried out as in Examples 9 to 13 (a).

The reaction discharge was analyzed by gas chromatography, the compositions stated in Table 4 being determined.

TABLE 4

| Example | Catalyst | Molar ratio MEA/EO | Temp./ °C. | Selectivities/% | |
|---|---|---|---|---|---|
| | | | | DEA | TEA |
| 11 | 3 | 4 | 110 | 90 | 10 |
| C2 | Autocatalysis | 4 | 110 | 86 | 14 |

The Comparative Example denoted by C2 was carried out without addition of a catalyst.

(c) Combination of the Processes for Selective MEA Synthesis According to (a) with the Process for the Selective Preparation of Diethanolamine According to (b)

Table 5 shows the results of experiments which were achieved in a combination process using two reactors.

TABLE 5

| Example | Catalyst I | Catalyst II | Temp./ °C. Reactor 1/2 | Selectivities | |
|---|---|---|---|---|---|
| | | | | DEA | TEA |
| 12 | Dowex ® 50X8 | 3 | 100/110 | 91 | 9 |
| 13 | 4 | 3 | 95/110 | 91 | 9 |
| C3 | Dowex ® 50X8 | Autocatalysis | 110/110 | 87 | 13 |

We claim:

1. A process for selectively preparing monoethanolamines by reacting ethylene oxide with ammonia in the presence of a catalyst in a tube reactor, wherein a feed gas stream containing ethylene oxide and ammonia is fed to the tube reactor and a product mixture (I) containing monoethanolamine, diethanolamine and triethanolamine is obtained, wherein the maximum temperature in the tube reactor is in the range of from 60 to 130° C. and said maximum temperature is from 0 to 30° C. above the temperature of the feed gas stream, wherein the reaction is carried out at a pressure of from 20 to 250 bar, wherein the molar ratio of ammonia to ethylene oxide in the feed gas stream is from 100:1 to 5:1.

2. The process of claim 1, wherein the temperature in the tube reactor is established by regulating along the tube reactor the heat flow from the reaction space or into the reaction space.

3. The process of claim 1, wherein the catalyst is a zeolite catalyst.

4. The process of claim 1, wherein the catalyst is water.

5. A process for the selective preparation of diethanolamines and/or triethanolamines, wherein monoethanolamine is prepared according to the process of claim 1 in a first reaction stage, monoethanolamine is separated from the product mixture (I) obtained thereby, and monoethanolamine is reacted with ethylene oxide in the presence of a catalyst in a tube reactor in a second reaction stage, wherein the feed gas stream containing monoethanolamine and ethylene oxide is fed to the tube reactor and a product mixture (II) containing diethanolamine and triethanolamine is obtained, wherein the maximum temperature in the tube reactor is in the range of from 60° C. to 140° C. in the second reaction stage, wherein the second reaction stage is carried out at a pressure of from 20 to 250 bar, wherein the molar ratio of monoethanolamine to ammonia in the feed gas stream is from 10:1 to 2:1.

6. The process of claim 1 wherein the molar ratio is 20:1 to 5:1 and the residence time of the reaction in the reactor is from 2 to 20 minutes.

7. The process of claim 2, wherein the molar ratio of ammonia to ethylene oxide in the feed stream is 20:1 to 5:1, the reaction is carried out at a pressure at from 70 to 160 bar, the residence time of the reaction in the reactor is from 2 to 20 minutes and the catalyst is a zeolite catalyst or water.

8. A process for selectively preparing monoethanolamines, diethanolamines or triethanolamines through control of reaction conditions, comprising selectively preparing monoethanolamine by feeding a gas stream containing ethylene oxide and ammonia to a first stage of a tube reactor wherein a product mixture (I) containing monoethanolamine, diethanolamine and triethanolamine is obtained, wherein the maximum temperature in the tube reactor is in the range of from 60 to 130° C. and said maximum temperature is from 0 to 30° C. above the temperature of the feed gas stream, and optionally selectively preparing diethanolamines or triethanolamines by further reacting a whole or part of the monoethanolamine from the product mixture (I) with ethylene oxide in the presence of a catalyst in the tube reactor, wherein the feed gas stream containing monoethanolamine and ethylene oxide is fed to the tube reactor and a product mixture (II) containing diethanolamine and triethanolamine is obtained, wherein the maximum temperature in the tube reactor is in the range of from 60° C. to 140° C. in the second reaction stage.

9. A process as claimed in claim 8, wherein selectively preparing the diethanolamines or triethanolamines occurs in a second process stage, and wherein the feed gas stream containing the ethylene oxide and monoethanolamine from mixture (I) is fed to the second process stage.

10. A process as claimed in claim 9, wherein the monoethanolamine is separated from the product mixture (I) before reacting with the ethylene oxide.

11. A process as claimed in claim 10, wherein the selectivity of the reaction is regulated by specifically controlling temperature profile in the reaction space.

12. A process as claimed in claim 11, wherein a higher temperature profile is used for selectively preparing the diethanolamine and a lower temperature is used for preparation of the monoethanolamine.

13. A process arranged to provide an option for selectively preparing monoethanolamine or diethanolamine and triethanolamine comprising selectively preparing monoethanolamine by feeding a gas stream containing ethylene oxide and ammonia to a first stage of a tube reactor wherein a product mixture (I) containing monoethanolamine, diethanolamine and triethanolamine is obtained, wherein the maximum temperature in the tube reactor is in the range of from 60 to 130° C. and said maximum temperature is from 0 to 30° C. above the temperature of the feed gas stream, or optionally selectively preparing diethanolamines or triethanolamines in a second stage comprising separating monoethanolamine from the product mixture (I), and a whole or part of the monoethanolamine is reacted with ethylene oxide in the presence of a catalyst in a tube reactor in a second reaction stage, wherein the feed gas stream containing monoethanolamine and ethylene oxide is fed to the tube reactor and a product mixture (II) containing diethanolamine and triethanolamine is obtained, wherein the maximum temperature in the tube reactor is in the range of from 60° C. to 140° C. in the second reaction stage.

* * * * *